US007170072B2

(12) United States Patent
Schwarz et al.

(10) Patent No.: US 7,170,072 B2

(45) Date of Patent: Jan. 30, 2007

(54) PACKAGING SYSTEM FOR RADIOACTIVE MATERIALS

(75) Inventors: Uwe Schwarz, Braunschweig (DE); Joachim Kahl, Braunschweig (DE)

(73) Assignee: AEA Technology QSA GmbH, Braunschweig (DE)

( * ) Notice: Subject to any disclaimer, the term of this patent is extended or adjusted under 35 U.S.C. 154(b) by 0 days.

(21) Appl. No.: 10/966,490

(22) Filed: Oct. 15, 2004

(65) Prior Publication Data

US 2005/0224728 A1 Oct. 13, 2005

(30) Foreign Application Priority Data

Mar. 30, 2004 (DE) .................. 20 2004 005 010 U

(51) Int. Cl.
*A61L 15/00* (2006.01)
*G21F 5/00* (2006.01)

(52) U.S. Cl. ............................... 250/507.1; 250/506.1; 206/438

(58) Field of Classification Search .............. 250/507.1
See application file for complete search history.

(56) References Cited

U.S. PATENT DOCUMENTS 3,673,411 A * 6/1972 Glasser ..................... 250/506.1
4,851,702 A * 7/1989 Perlman .................. 250/507.1
5,834,788 A * 11/1998 Fu et al. .................. 250/506.1

* cited by examiner

*Primary Examiner*—Nikita Wells
*Assistant Examiner*—James J. Leybourne
(74) *Attorney, Agent, or Firm*—Akerman Senterfitt; Stephan Pendorf; Yonghong Chen

(57) ABSTRACT

Packaging system for radioactive materials having: a vial with closure for accommodating the radioactive material; a first casing to be opened, enclosing the vial, and essentially made from a transparent material, which has a capture cross-section selected for shielding at least a part of the emitted radiation; and a second casing to be opened, made from a material with a high capture cross-section (Z) for essentially shielding the remaining radiation, the second casing enclosing the first casing.

26 Claims, 3 Drawing Sheets

(a) (b)

(a) (b)

(a)

(b)

PACKAGING SYSTEM FOR RADIOACTIVE MATERIALS

FIELD OF THE INVENTION

The present invention relates to packaging systems for radioactive materials, in particular radioactive solutions. In one special embodiment, the present invention relates to packaging systems for injectable diagnostics or drugs.

BACKGROUND TO THE INVENTION

Packaging systems for drugs and diagnostics are controlled by strict requirements under drugs legislation, both in terms of material compatibility and with regard to ability to sterilize. This applies in particular to injectable preparations and diagnostics. For example, no elements of the packaging used must be soluble in the solution to be packaged. Furthermore, the container must be such that it can be adequately sterilized before the contents are removed.

Consequently, it is standard practice to package injectable drug preparations either in solid glass vials closed by fused ends or glass vials which can be closed by means of a stopper and optionally a flanged cap. In the latter case, the contents are usually removed by piercing a septum or the actual stopper with the syringe and drawing the solution into the syringe with the stopper closed. In order to prevent any form of contamination, the cover region must therefore be sterilized beforehand. This is done by spraying and/or wiping with ethanol solutions.

In addition to these requirements intended to regulate the drug aspect, containers for radioactive materials, including radioactive solution, are subject to additional requirements with regard to containment of the emitted radiation. For transport purposes, therefore, radioactive materials are usually placed in a first packaging which is sealed. For containment purposes, this packaging is in turn placed in a lead container which acts as the actual shield. In the past, however, this type of packaging has proved to be impractical, specifically in the case of injectable drug preparations.

Vials of the type that are closed by fusion are totally unsuitable for packaging radioactive materials due to the risk of the syringe becoming contaminated when the vial end is broken off in order to open them. If glass vials sealed by stoppers are used, they usually have to be completely removed from the lead container, which means that the doctor handling them is exposed to what is usually a considerable amount of radiation, depending on the radiation emitted. The same risk of exposure exists, at least in the region of the tips of the fingers by which the vials are held, even in the case of (β-radiation, which is usually shielded by a few centimeters of air. This is also not acceptable for those who constantly handle radio-chemicals and radioactive drugs.

With the packaging systems used to date, therefore, it is not possible to provide shielding and permit removal of the contents with a visual control simultaneously. The sealed container has to be removed form the lead container so that the doctor can completely remove the entire solution from the vessel and visually check the removal process.

In order to get round this problem, a container has been used for radioactive solutions in the past, in which a vial or another container such as an Eppendorf container is placed in a casing of Plexiglass. The container is closed with a screw cap so that a rubber seal placed on the glass vial is pressed onto the glass vial by the screw cap and is sealed by it as a result. However, this system does not meet the requirements of current drug legislation. For one thing, impurities are able to get into the solution from the screw thread, simply by turning it. Secondly, there is no guarantee that the rubber seal will remain on the opening of the glass vial when the cap is unscrewed, thereby removing the contact pressure. More specifically, this type of packaging does not allow the container serving as the shield and the actual seal of the radioactive solution to be opened separately. In addition, the seal can not be adequately sterilized if left in place. The same applies to sterilization of the screw thread. Finally, radioactive contamination of the ambient environment can not be ruled out if the seal falls out.

The present invention is intended as a means of overcoming the problems of the prior art outlined above.

SUMMARY OF THE INVENTION

The present invention relates to a packaging system for radioactive materials comprising, starting from the inside working outwards: (i) a vial with a closure for receiving the radioactive material, (ii) a first casing to be opened, which encloses the vial and is essentially made from a transparent material and has an appropriate capture cross-section for shielding at least a part of the emitted radiation, and (iii) a second casing to be opened, made from a material with a high capture cross section (Z) for essentially shielding the remaining radiation, the second casing enclosing the first casing.

Other preferred embodiments are defined in the dependent claims.

DETAILED DESCRIPTION OF THE INVENTION

Figure 1:
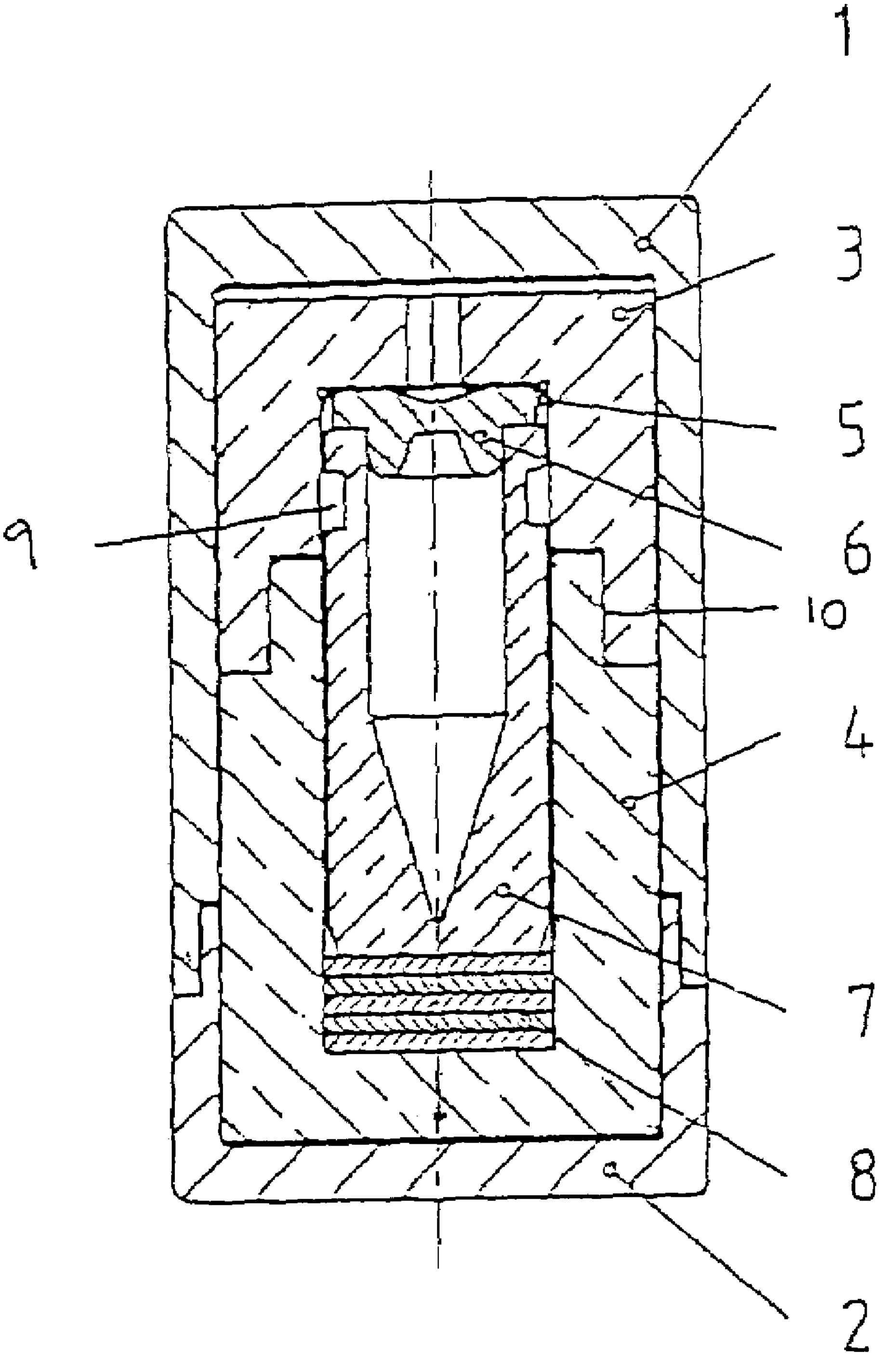
FIG. 1 is a longitudinal section through a preferred embodiment of the packaging system proposed by the invention.
Figure 2:
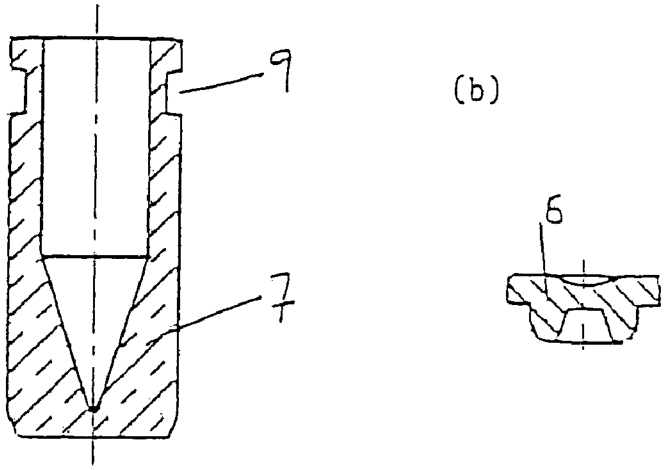
FIG. 2 is a longitudinal section of the vial illustrated in FIG. 1.
Figure 3:
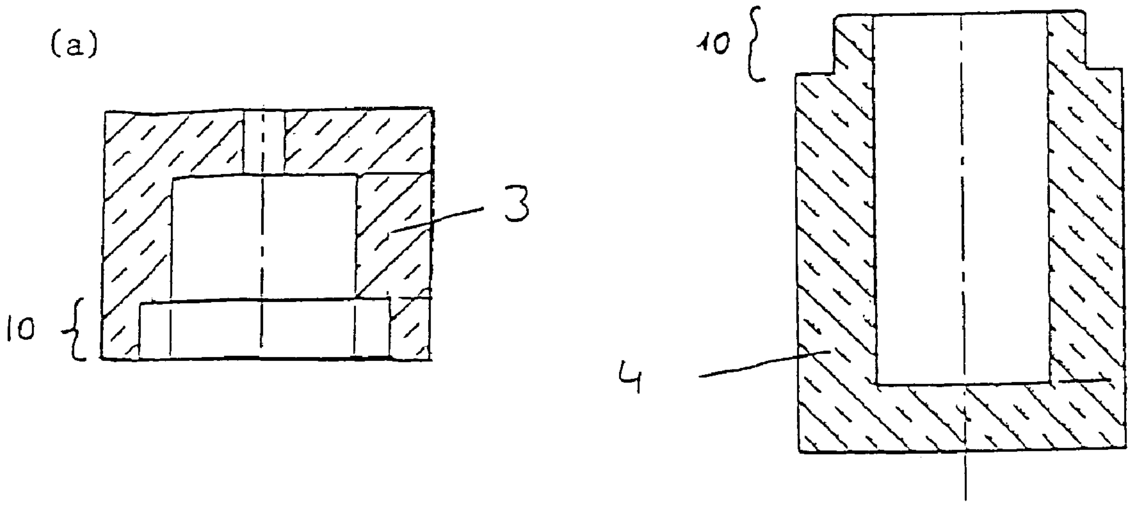
FIG. 3 is a longitudinal section through the first casing illustrated in FIG. 1.
Figure 4:
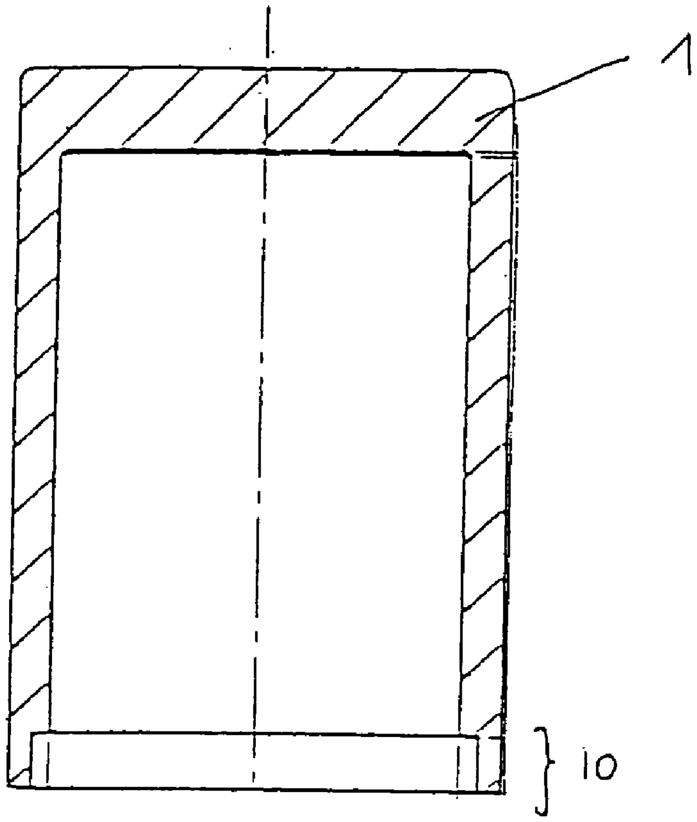
FIG. 4 is a longitudinal section through the second casing illustrated in FIG. 1.
Figure 4:
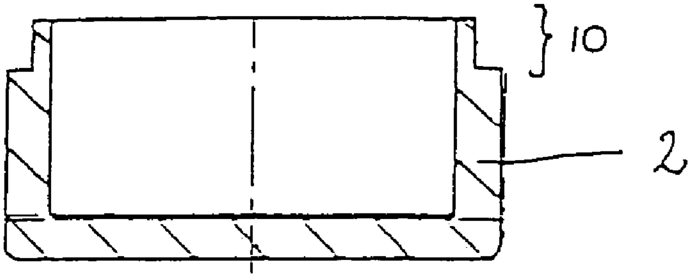

The packaging system proposed by the invention comprises (i) a vial, (ii) a first casing and (iii) a second casing, each of which is opened separately and independently of the others.

In the packaging system proposed by the invention, the second casing (1, 2) assumes the shielding function as such. However, a part of this shielding function is assumed by the first casing (3, 4). The two casings can be opened separately and independently of one another. Once the second casing has been opened, however, its shielding function ceases. However, a part of it is still contained by the first casing.

Due to the fact that the vial proposed by the invention has its own separate closure, the radioactive material is still sealed in the vial, even after the two casings have been opened. The vial closure, which might be a stopper (6) and flanged cap (5) for example, can now be sterilized in the same way as a conventional drug vial and pierced by a syringe in order to remove the solution after sterilization.

Since the first casing proposed by the invention is made from a transparent material, it does not have to be removed in order to check that it has been completely emptied. An at least partial shield against the emitted radiation is therefore provided, even whilst the contents are being removed. The problems known from the prior art can therefore be resolved and overcome by using a vial with a closure and two casings, the first of which his made from a transparent material and has a large enough capture cross-section to shield at least some of the emitted radiation, and the second of which is made from a material with a high capture cross-section (Z) which essentially shields the remaining radiation.

In principle, the first casing (3, 4) may be of any appropriate shape suitable for accommodating the vial with closure (5, 6, 7). Possible cross-sections and/or longitudinal sections are square, rectangular, polyhedral, oval or circular, for example, and the sections through the casing in planes extending perpendicular to one another need not be identical. For example, cylindrical, cube or cuboid shapes are possible, although cylindrical shapes are preferred. Likewise, the external shape of the first casing and the shape of the interior accommodating the vial and closure need not be identical, although this is preferred.

A preferred embodiment is one in which the first casing is provided in the form of a cylinder, which is preferably closed at one or both ends by thicker glass plates. Although not strictly necessary, it is preferable if the glass plate(s) is or are made from the same material as the respective cylinder wall.

The first casing is essentially made from a transparent material. This material has a capture cross-section (Z) suitable for shielding at least a part of the emitted radiation (e.g. β-radiation). This part might be a specific type of radiation. In the case of β-emitters such as Y-90, for example, the first casing may shield the originally emitted β-radiation completely, whereas the bremsstrahlung (usually γ-radiation) into which some of the β-radiation is already converted on passing through the vial wall, is not shielded by the first casing. Suitable materials for shielding β-radiation usually have a low atomic weight (for example carbon) and are known to the skilled person. Alternatively, the part to be shielded might be a desired part-quantity of the total radiation emitted. An example of this would be J-125 and the soft γ-radiation emitted by it. It can be shielded to a desired percentage in the first casing already, for example by selecting lead glass, in which case the rest of the radiation is shielded by the second casing.

The skilled person will be able to calculate or conduct routine tests to determine the thickness of the first casing needed to obtain the desired shielding depending on the selected material, emitted radiation and dose, as well as the tolerable residual radiation. The material used for the first casing is preferably a transparent plastic. In an even more preferred embodiment, the thickness is sufficient to provide a complete shield against the β-radiation emitted by the radioactive material. The material thickness or wall thickness of the casing need not be identical over the entire casing, but may vary.

Basically, any material that is sufficiently transparent with an appropriate capture cross-section and has the required resistance to the emitted radiation may be used. A transparent plastic is preferred, although other materials such as quartz or glass (for example lead glass) may also be used. The plastic is preferably selected from the group consisting of polyethylene, polypropylene, polycarbonate, polystyrene, polyethylene terephthalate, polyacrylate, polymethacrylate, in particular Plexiglass or lead Plexiglass, and copolymers containing them and mixtures thereof. The materials listed above are given by way of illustration only.

In the embodiment most particularly preferred, the first casing (3, 4) encases the vial (7), and optionally an insert (8) placed underneath the base of the vial, in a tight fit. First of all, a tight-fitting enclosure will prevent the vial from sliding around in the container, which might result in damage. Furthermore, this enables the best possible use to be made of the material.

An insert may be provided underneath the vial. One reason for providing this is that it can absorb any solution which might escape from the vial. It may also be provided as a means of cushioning cavities in the interior of the first casing, thereby enabling vials of different sizes to be accommodated in a standard casing, i.e. vials of different heights.

As with the first casing, the second casing (1, 2) enclosing the first casing may basically be of any appropriate shape. Suitable cross-sections are square, rectangular, polyhedral, oval or round and round cross-sections are preferred. Other cross-sections would also be possible, however. Also, longitudinal sections through the casing need not necessarily be identical in planes perpendicular to the cross-sectional plane. Accordingly, cube, cuboid, polygonal or cylindrical shapes are possible and the preferred shape is cylindrical. The external shape of the second casing and the shape of the interior needed to accommodate the first casing and the vial contained in it need not be identical.

The second casing is preferably also a cylinder, which is closed at both ends, preferably by cover plates. The cover plate(s) of the second cylinder is or are preferably made from the same material as the cylinder wall. However, this is not compulsory.

The second casing is made from a material with a high capture cross-section (Z) for essentially shielding the remaining radiation and encases the first casing. Most preferably, the second casing encloses the first casing in a tight fit. This means that the interior of the second casing matches the shape of the first casing. If using a cylindrical design for both the first and the second casing, the internal diameter of the second casing is bigger than the external diameter of the first casing by no more than is needed to enable the first casing to slide easily in and out of the second cylinder and to enable the cap to be easily removed from the second cylinder, see below. The height of the interior of the second casing therefore corresponds to the height of the first casing.

The second casing is preferably made from a metal or a metal alloy with a high Z. By a high Z is meant a high capture cross-section for the type of radiation in question. The thickness of the second casing is selected so that it is essentially sufficient to shield the remaining radiation completely. The material thickness or wall thickness of the casing need not be identical over the entire casing, but may vary. The skilled person will be in a position to select the most appropriate thickness for both casings, which may be calculated or determined by simple routine experiments.

Most preferred is a metal or metal alloy from the group consisting of Al, Ag, Au, Pb, Cd, Ce, Cr, Co, Cu, Fe, Hg, Hf, Bi, In, Mg, Mn, Mo, Nb, Ni, Pd, Pt, Pr, Re, Rh, Sn, Si, Ta, Ti, Tb, Th, V, W, Y, Yb, Zn, Zr, Al/Mg, Al/Cu, Al/Cu/Mg, Al/Mg/Si, Al/Cr, Tinal alloy BB, copper alloys such as brass and bronzes, iron alloys such as Fe/Cr, Fc/Ni, Fe/Cr/Ni, Fe/Cr/Al, nickel alloys Ni/Ti, Ni/Cr, and Nitinol, platinum alloys, titanium alloys such as Ti/Al, Ti/Al/V and Ti/Mo, Woods alloys, Inconel, tungsten alloys such as Densimed and mercury alloys such as amalgams. Most especially preferred are lead or the tungsten alloy, Densimed.

The first casing (3, 4) may be opened by removing a cover (3) so that a top part of the vial (7) is exposed when the casing is opened. Preferably the proportion of vial exposed is such that, although sterilization or some other manipulation such as removing the vial using tweezers or a gripper arm is possible, the vial body remains largely covered in order to guarantee continued shielding. If a commercially available primary packaging system for injection solutions is used as the vial (a glass vial of hydrolytic class I as specified in the drugs compendium), the top edge, including stopper (6) and flanged cap (5) and the groove (9) underneath it, is exposed to permit manipulation of the vial.

In one particularly preferred embodiment, the first casing is provided in the form of a cylinder closed by at least a top cover plate. The cover (3) which is removed to open the first casing (3, 4) then comprises the top cover plate and a part of the cylindrical wall. The distance of the opening from the top cover plate is shorter than the distance of this opening from the bottom cover plate when the cap is removed. The distance of the opening from the top cover plate is preferably selected so that the opening is disposed directly underneath the groove (9), by reference to the vial contained in the casing, to permit manipulation. Conversely, when the cover has been removed, the entire vial body preferably remains essentially covered by the first casing. This will guarantee continued shielding.

The second casing (1, 2) may also be opened by removing a cover (1). The second casing is preferably opened in such a way that once it has been opened, essentially the entire vial is visible through the transparent first casing. If the second casing is provided in the form of a cylinder closed by cover plates, the cover (1) preferably comprises the top cover plate and a (predominant) part of the cylindrical wall. By contrast with the first casing, the distance of the opening from the cover plate which results when the cover is removed is bigger than the distance of this opening from the bottom cover plate. Consequently, when the cover of the second casing is removed, a predominant or major part of the first casing, and through it the vial, is visible.

In one very particularly preferred embodiment, once the second casing (1, 2) has been opened by removing the cover (1), only the bottom cover plate and optionally a smaller part of the second casing remains behind on the packaging system. This design differs significantly from conventional packaging systems in which the cover removed is usually only small.

To facilitate the opening processes, the first and/or the second casing may have mating shoulders (10) or a thread. For technical reasons pertaining to the material used, it is preferable for the second casing to have a mating shoulder, especially if it is made from lead. It is also preferable to provide a mating shoulder for the first casing in order to keep the possibility of contamination as low as possible. Other types of opening designs are possible and should not be ruled out. If necessary, both casings may be sealed by means of an adhesive tape at their openings, for example.

The first and the second casing may be fixedly joined to one another, at least in the region of the bottom cover plate. Adhesive, welding, etc., may be used for this purpose. However, the join must not be such that it prevents the first and second casing from being opened independently. Other designs are possible in which the second cover has a bottom cover plate and the cylindrical wall of the first casing is secured to the internal face of the bottom cover plate of the second casing. In this case, because the first casing does not have a bottom cover plate, shielding in the lower region of the container is therefore provided by the second casing only. Alternatively, the first casing may have a bottom cover plate, also made from metal, in order to provide a more intensive shield in this region.

In one very particularly preferred embodiment, the first casing may be provided in the form of a cylinder closed by at least a top cover plate and the cover plate has a cut-out or orifice above the stopper of the vial, which is centrally disposed in most cases. This being the case, the radioactive material, in particular a solution, may be removed by introducing a cannula into the orifice in the first casing and piercing the stopper. With this embodiment, the doctor or person handling the system is guaranteed maximum shielding by means of the first casing, whilst simultaneously allowing removal of the contents to be visually observed. Preferably, the orifice in the cover plate of the first case is dimensioned so that the syringe body can be seated on it in a tight fit.

If desirable, the vial closure of this embodiment can be sterilized before the contents are removed. To this end, the cover of the first casing may be briefly lifted, sprayed with an ethanol solution and wiped and the cover of the first casing put back in place. Only then are the contents removed.

The vial used for the purposes of the invention can be closed separately. This separate closure enables the first and second casing to be opened without rendering the radioactive material contained in the vial directly accessible. On the contrary, once both casings have been opened, the contents of the vial can be drawn off without any risk of the radioactive material escaping and thus contaminating the ambient environment.

In principle, the vial may be made from any appropriate material. It is preferably a transparent material. For example, all the materials specified above for the first casing are suitable in principle. More preferably, the vial is made from glass or quartz. The choice is made depending on the material to be packaged and the radiation to be shielded. The vial may be a vial with a pointed base or a vial with a flat base and the choice will depend on the material to be packaged and its volume. The dimensions of the vial are usually adapted to the volume to be packaged, which is between 1 and 25 ml, preferably 1 and 5 ml, depending on the intended purpose of the packaging system. However, smaller or larger capacities are not ruled out. The vial with closure is most preferably a so-called primary packaging system for drugs. Commercially available glass vials such as those of hydrolytic category I as specified in the drugs compendium may be used. Their use is preferred. Specifically, this is a glass vial closed by a stopper of plastic, preferably a rubber material, and optionally a flanged cap. However, other closures (stopper only), screw-on cap, etc., would also be conceivable.

Basically, the radioactive materials to be packaged in the inventive packaging system may be any type of radioactive material. These materials are preferably selected from the group consisting of solutions, powder, particles, granulate, lyophilisate, liposomes, nano-particles, emulsions or suspensions of radioactive nuclides or compounds containing them, salts or alloys. They are preferably salts, oxides, fluorides, organic compounds, complexes or bio-molecules marked with nuclides such as nucleic acids, proteins, antibodies, sugars, lipids, etc. The radioactive materials are preferably solutions, emulsions or suspensions. Alternatively, a dry substance may be contained in the packaging system, such as powder, liposomes or lyophilisates, which is converted into such a solution, emulsion or suspension prior to use.

The radioactive materials used for the purposes of the invention are preferably selected from β-emitters, γ-emitters and/or X-radiation emitting materials, which preferably contain a maximum particle quantity of at least 500 keV in the case of β-emission ($E_{\beta max}$) and/or a photon energy in the range of from 20 to 100 keV in the case of γ-radiation and/or X-radiation. More especially preferred are the nuclides Sr-90, Y-90, Y-86, Sr-89, Tm-170, P-32, Ca-45, Cl-36, Ce-144, Tb-160, Tb-182, Tl-204, W-188, Re-188, Ir-192, Pd-103, Se-75, J-125, S-35, Lu-177, Ho-166, Re-186, Te-125m, Te-99m or mixtures thereof. Yttrium-90 is most especially preferred.

The packaging system proposed by the invention may be used for transporting and/or storing radioactive materials for the short-term and medium-term. The respective activity will depend on the selected materials and wall thickness. In the case of a wall thickness of 4 mm of lead or 1 cm of Plexiglass, for example, up to 100 GBq of Y-90 (in a solution of up to 10 ml) can be packaged.

EXAMPLE

The packaging system proposed by the invention will be explained on the basis of examples illustrated in FIGS. 1 to 4 of the appended drawings.

FIG. 1 illustrates a preferred embodiment of the packaging system proposed by the invention in the assembled form. FIG. 2*a* shows a standard conventional packaging means for drugs, comprising a glass vial with a 20 mm external diameter, 12.6 mm internal diameter and a height of 47.5 mm. This glass vial has a groove approximately 1 mm below the top edge, which enables a flanged cap to be located or permits manipulation with tweezers, for example.

The vial may be closed by the stopper illustrated in FIG. 2*b*, which is usually made from a rubber material. The stopper has a cover diameter which extends beyond the internal diameter of the glass vial and has a circular raised area on the bottom face directed towards the interior of the vial, which lies against the internal wall of the vial in the closed state, thereby providing the closure. If desired, the stopper may be additionally secured by means of a flanged cap (5) which locates in the groove (9) on the vial.

As illustrated in FIGS. 1 and 3*a/b*, the first casing has a base (4) and a cover (3), comprising a cylinder provided with cover plates. The cylinder has a cylindrical interior, in which the glass vial can be placed in a tight fit, optionally with the aid of an underlying insert (8).

The first casing (3, 4) is made from Plexiglass and has a wall thickness of approximately 9 mm. To accommodate the glass vial, the cylinder has an internal diameter of 21 mm and accordingly an external diameter of 39 mm. The total height of the cylindrical casing is approximately 83 mm and it has a mating shoulder (10) with an outwardly lying overdub of approximately 7 mm at a height of approximately 30 mm from the top cover edge. As may be seen from FIG. 1, the mating shoulder is designed so that the casing base (4) incorporates the inwardly lying web abutting with the vial, which remains in place when the casing is opened by removing the cover (3) and thereby continues to provide a shielding effect. When the cover is removed, the vial is exposed to a point just below the bottom edge of the groove (9). This enables the vial to be manipulated and optionally opened and/or removed from the packaging system with the aid of gripper arms, fingers or tweezers, for example.

As may be seen from FIGS. 1 and 4*a/b*, the second casing in this example is also cylindrical in shape. This casing is made from lead. The cylindrical wall in this example is approximately 4 mm thick and the base and cover plates are of approximately the same thickness, although they may also be thicker. The internal diameter of the second cylindrical casing is 40 mm, as a result of which it is able to accommodate the first casing in the tightest possible fit. The height of the cylinder outside is approximately 95 mm and the height of the interior is slightly in excess of the height of the first casing.

The second casing may also be opened by removing the cover (1) from the base (2). In this case, mating shoulders (10) are also provided for opening purposes, but at a distance of approximately 71 mm from the top edge of the cover plate. Consequently, when the cover is removed, the entire first casing is essentially removed and only its base (2) is left behind in the packaging system. The mating shoulders, as with the first casing, are designed so that when the mating shoulder is open, a web is left behind abutting with the first casing. However, when the cover (1) is removed, the entire vial (7) is essentially exposed so that the removal of the radioactive material from its interior can be visually observed.

The base (4) of the first casing is adhered to the base (2) of the second casing. This prevents the first casing base from sliding or falling out of the second casing base. However, this fixing is not compulsory.

With the selected wall thickness of 9 mm for the Plexiglass, the entire β-radiation emitted from the yttrium-90 solution can be shielded. The remaining γ-radiation is totally shielded by the second casing (1, 2) in the closed state.

What is claimed is:

1. A packaging system for radioactive materials, which comprises, starting from the inside and working outwards:

(1) a vial with closure for accommodating the radioactive material, (ii) a first casing to be opened, enclosing the vial, and essentially made from a transparent material, which has a sufficient or appropriate capture cross-section for shielding at least a part of the emitted radiation, and (iii) a second casing to be opened, made from a material with a high capture cross-section (Z) for essentially shielding the remaining radiation, the second casing enclosing the first casing, wherein the second casing can be opened by removing the cover so that when the casing is opened, the entire vial is essentially visible through the transparent first casing.

2. The packaging system as claimed in claim 1, in which the first casing is provided in the form of a cylinder, which is closed by cover plates at one or both ends.

3. The packaging system as claimed in claim 1, in which the second casing is provided in the form of a cylinder, which is closed by cover plates at both ends.

4. The packaging system as claimed in claim 1, in which the first casing encloses the vial in a tight fit.

5. The packaging system as claimed in claim 1, in which the second casing encloses the first casing in a tight fit.

6. The packaging system as claimed in claim 2, in which the cover plate(s) of the first is or are respectively made from the same material as the respective cylinder wall.

7. The packaging system as claimed in claim 1, in which the first casing can be opened by removing a cover and a top part of the vial is exposed when the casing is opened.

8. The packaging system as claimed in claim 7, in which the first casing is provided in the form of a cylinder closed by at least a top cover plate, the cover comprises the top cover plate and a part of the cylinder wall and the distance of the opening from the top cover plate is shorter than the distance of this opening from the bottom cover plate when the cover is removed.

9. The packaging system as claimed in claim 1, in which the second casing is provided in the form of a cylinder closed by cover plates, the cover comprises the top cover plate and a part of the cylinder wall and the distance of the opening from the top cover plate is greater than the distance of this opening from the bottom cover plate when the cover is removed.

10. The packaging system a claimed in claim 9, in which only the bottom cover plate of the second casing is essentially left on the packaging system when the second casing is opened by removing the cover.

11. The packaging system for as claimed in claim 1, in which the first and/or second casing has a mating shoulder or a thread.

12. The packaging system as claimed in claim 1, in which the vial is made from glass.

13. The packaging system as claimed in claim 1, in which the vial is a vial with a pointed base or a vial with a flat base.

14. The packaging system as claimed in claim 1, in which the vial is a primary packaging means authorized for drugs.

15. The packaging system as claimed in claim 1, in which the vial is closed by a stopper.

16. The packaging system as claimed in claim 1, in which the first casing is made from a transparent plastic of a sufficient thickness essentially to shield a β-radiation emitted by a radioactive solution.

17. The packaging system as claimed in claim 16, in which the plastic is selected from the group consisting of polyethylene, polypropylene, polycarbonate, polystyrene, polyethylene terephthalate, polyacrylate, polymethacrylate, copolymers containing them and mixtures thereof.

18. The packaging system as claimed in claim 1, in which the second casing is made from a metal or a metal alloy with a high Z of a sufficient thickness essentially to shield the remaining radiation completely.

19. The packaging system as claimed in claim 18, in which the metal or metal alloy is selected from the group consisting of Al, Ag, An, Pb, Cd, Ce, Cr, Co, Cu, Fe, Hg, Hf, Bi, In, Mg, Mn, Mo, Nb, Ni, Pd, Pt, Pr, Re, Rh, Sn, Si, Ta, Ti, Tb, Th, V, W, Y, Yb, Zn, Zr, Al/Mg, Al/Cu, Al/Cu/Mg, Al/Mg/Si, Al/Cr, Tinal alloy BB, copper alloys such as brass and bronzes, iron alloys such as Fe/Cr, Fe/Ni, Fe/Cr/Ni, Fe/Cr/Al, nickel alloys Ni/Ti, Ni/Cr, and Nitinol, platinum alloys, titanium alloys such as Ti/Al, Ti/Al/V and Ti/Mo, Woods alloys, Inconel, tungsten alloys such as Densimed and mercury alloys such as amalgams.

20. The packaging system as claimed in claim 1, in which the first casing has a cut-out above the closure of the vial.

21. The packaging system as claimed in claim 20, in which the first casing is provided in the form of a cylinder closed by at least a top cover plate, which has a centrally disposed opening.

22. The packaging system as claimed in claim 1, in which these materials are selected from the group consisting of solutions, powder, particles, granulate, lyophilisate, liposomes, nano-particles, emulsions or suspensions.

23. The packaging system as claimed in claim 1, in which the radioactive materials are selected front β-emitters, γ-emmiters and/or X-radiation emitting material, which has a maximum particle energy of at least 500 keV in the case of β-radiation ($E_{\beta max}$) and/or a photon energy in the range of from 20 to 100 keV in the case of γ-radiation and/or X-radiation.

24. The packaging system as claimed in claim 23, in which the radioactive material contains the nuclides Sr-90, Y-90, Y-86, Sr-89, Tm-170, P-32, Ca-45, Cl-36, Ce-144, Tb-160, Ta-182, Tl-204, W-188, Re-188, Ir-192, Pd-103, Se-75, J-125, S-35, Lu-177, Ho-166, Re-186, Te-125m, Tc-99m or mixtures thereof.

25. The packaging system as claimed in claim 1, in which the first casing encloses the vial and a bottom insert disposed underneath the base of the vial in a tight fit.

26. The packaging system as claimed in claim 1, in which the vial is closed by a stopper and a flanged cap.

* * * * *